(12) United States Patent
Osaheni et al.

(10) Patent No.: US 6,193,412 B1
(45) Date of Patent: Feb. 27, 2001

(54) METHOD FOR MEASUREMENT OF THE SURFACE POLARITY OF INORGANIC MATERIAL

(75) Inventors: John Aibangbee Osaheni, Clifton Partk; Stanlee Teresa Buddle, Gloversville, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/259,666

(22) Filed: Feb. 26, 1999

(51) Int. Cl.[7] ....................................................... G01N 25/20

(52) U.S. Cl. .................................................................. 374/45

(58) Field of Search ................................. 374/45; 73/866

(56) References Cited

U.S. PATENT DOCUMENTS

| | | | |
|---|---|---|---|
| 4,554,147 | 11/1985 | Stoll et al. | 423/335 |
| 5,652,017 | 7/1997 | Osaheni et al. | 427/212 |
| 6,028,236 | * 2/2000 | Toulhoat et al. | 585/15 |
| 6,093,236 | * 7/2000 | Klabundle et al. | 95/128 |

* cited by examiner

*Primary Examiner*—Diego Gutierrez
*Assistant Examiner*—Stanley J. Pruchnic, Jr.
(74) *Attorney, Agent, or Firm*—Noreen C. Johnson; Douglas E. Stoner

(57) ABSTRACT

The present method comprises determination of surface polarity of an inorganic material by measurement of the net heat of inert gas adsorption on the material surface, preferably by measurement of the BET constant C. The analysis is fast and easy to execute, and provides high signal-to-noise ratio. It is applicable to many surfaces, such as those containing silanol groups, regardless of the nature of the hydrophobic groups used in surface treatment of the material.

16 Claims, 2 Drawing Sheets

METHOD FOR MEASUREMENT OF THE SURFACE POLARITY OF INORGANIC MATERIAL

BACKGROUND OF THE INVENTION

The present invention relates to methods for the measurement of surface polarity of inorganic materials. In particular, the present invention relates to a method for the measurement of the surface hydrophobicity or hydrophilicity of inorganic material, particularly materials which have been surface treated.

Inorganic materials in particulate form, such as silica ($SiO_2$) and titania ($TiO_2$), are used as thixotropic agents and as fillers in materials as diverse as inks, resins, rubbers, circuit boards, paints, and cosmetics. An important use of silica and other inorganic powders is as fillers, i.e., as reinforcing agents for polymer matrices to form composites. Composites comprising particulate silica and silicone elastomers have found particular utility in household goods such as sealants, or in automotive and oven gaskets, electrical insulators and connectors, baby bottle nipples, and the like.

The reinforcing properties of fillers, and fumed silica in particular, are strongly dependent on their morphology and surface properties. Morphology is determined primarily by the synthetic method used to obtain the filler, whereas surface properties are determined primarily by surface polar groups, which render the fillers hydrophilic. In silica these polar groups are typically hydroxyl groups, most often present as silanol groups. To be effective as a filler in polymer systems, the filler surface may be treated to change its polarity. Typically, the fillers are rendered hydrophobic by such treatment. Typical methods for rendering silica hydrophobic are disclosed in U.S. Pat. Nos. 4,554,147 and 5,652,017 to Osaheni et al., wherein a silica powder is treated with a silylating agent comprising, for example, a polyorganosiloxane, triorganosilane, or diorganosilane. Differences in the number of surface polar groups, particularly surface hydroxyls, and/or the nature of hydrophobic groups on the surface of the filler after treatment will result in the filler having different characteristics.

In many applications it is critical to determine the degree of hydrophobicity of the powder fillers, in particular silica fillers. It is particularly important to ensure that treated fillers are consistent from batch to batch, in order to guarantee the properties and quality of the composite product.

Treated inorganic powders may be characterized by a series of tests, including thermogravimetric analysis combined with Fourier transform infrared analysis (TGA-FTIR) to determine the amount of physically absorbed species; carbon analysis; proton nuclear magnetic resonance ($^1H$ NMR) spectroscopy; and silicon-29 cross polarization and magic angle spinning nuclear magnetic resonance ($^{29}Si$ CP/MAS NMR) spectroscopy. Acid-base titrations can also be used, but are inaccurate where the residual titratable groups, such as silanols, are not readily accessible. Depending on the silylating agent, at least two or three of these analyses need to be performed in order to determine the hydrophobic nature of the inorganic powder. Such extensive analyses are expensive and time consuming. Accordingly, there remains a need in the art for accurate and efficient methods for measuring the surface polarity, in particular the surface hydrophobicity of inorganic materials, particulates, and powders.

SUMMARY OF THE INVENTION

The present method comprises a method for determination of surface polarity of an inorganic material by measurement of the net heat of inert gas adsorption on the material surface. The net heat of adsorption is then correlated with the concentration of residual surface polar groups, and thus reflects the degree of hydrophobicity of the inorganic material. The analysis is fast and easy to execute, and provides a high signal-to-noise ratio (standard deviation is generally less than or equal to 0.2). It is furthermore applicable to many surfaces, such as those containing hydroxyl groups, regardless of the nature of the hydrophobic groups used in surface treatment of the material.

DETAILED DESCRIPTION OF THE INVENTION

The method of the present invention comprises correlation and standardization of surface polarity of inorganic materials with measurement of the net heat of adsorption of an inert gas, in particular nitrogen, onto the surface of the inorganic material. More preferably, the net heat of adsorption of nitrogen on the material surface provides a reproducible way to measure the degree of hydrophobicity.

The inorganic material may be particulate or non-particulate material having surface areas in the range from about 0.1 $m^2/g$ to about 450 $m^2/g$. The method is particularly advantageous for measurement of the surface hydrophobicity of particulate materials having dimensions on the order of 1 nanometer to 100 microns. The shape of the inorganic material is not critical. It is to be understood that while the following description is directed to measurement of surface polarity, in particular the surface hydrophobicity of a commonly used filler material, fumed silica, the method is applicable to other inorganic materials having other purposes. Such materials include, but are not being limited to, precipitated silica, titania, powdered glass, silicates, alumina, asbestos, barium sulfate, zinc oxide, ferric oxide, zinc sulfide, silica fume, and the like. Such materials and their methods of manufacture are well known in the art.

Practice of the method of the present invention may rely on analysis of the isotherm generated by the adsorption of an inert gas, preferably nitrogen, onto the inorganic material at constant temperature. Although nitrogen is preferred, other inert gases, such as argon, krypton, helium, and carbon monoxide can be used in accordance with this invention. Although other analytical treatments may be applied, the analysis is most readily made using the BET equation, the model of Brunauer, Emmett, and Teller as described in the Journal of the American Chemical Society, Vol. 60, pp. 301–319 (1938). The BET equation is widely used to determine the specific surface area of fillers. This equation assumes that the heat of adsorption for the first layer of molecules adsorbed on the surface has a specific value, while the heat of adsorption of succeeding layers of molecules is equal to the heat of condensation of the liquid adsorbate (Equation 1):

$$\frac{P_s}{V_A(P_0 - P_s)} = \frac{1}{V_M C} + \frac{C-1}{V_M C} * \frac{P_s}{P_0} \quad (1)$$

wherein $V_M$ is the volume of gas adsorbed in a complete monolayer, $V_A$ is the volume of gas adsorbed, $P_S$ is sample pressure, $P_O$ is the saturation pressure, and C is a constant proportional to the net heat of adsorption.

Figure 1:
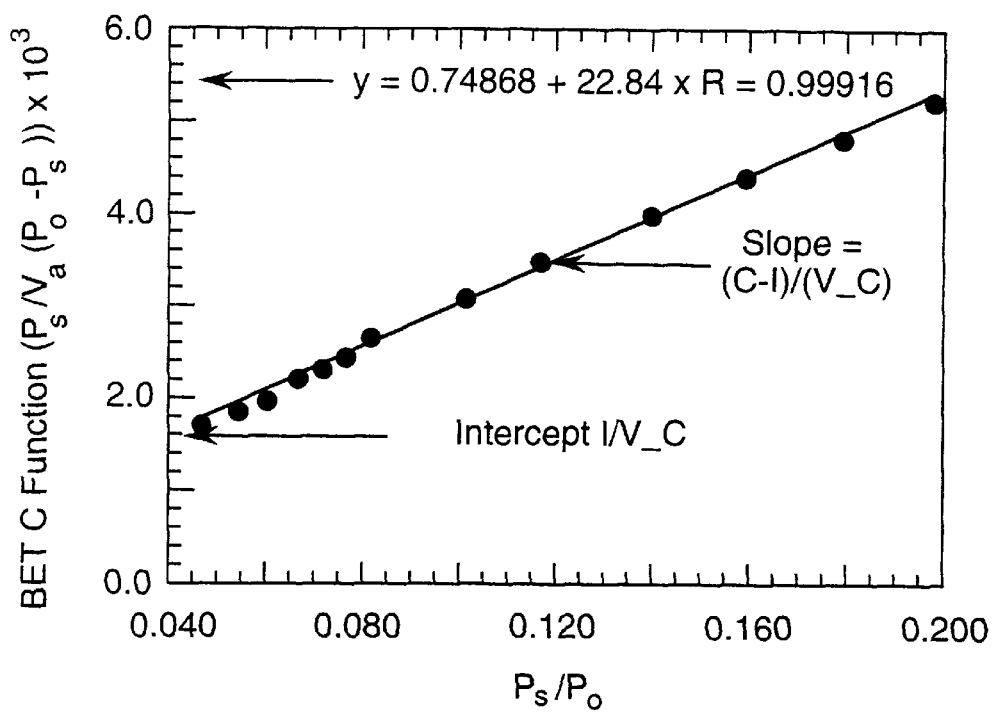
FIG. 1 illustrates determination of BET constant C.

The linear form of the BET equation represented in equation (1) is used to calculate graphically the constant C. Specifically, a plot of $$\frac{P_s}{V_A(P_0 - P_s)} \quad (2)$$

versus $(P_S/P_O)$ provides a straight line having the slope $(C-1)/V_M C$ and intercept $1/V_M C$ from which the constant C may be determined. FIG. 1 shows an example of determining the BET constant C graphically.

As shown in Equation 3, the BET constant C is an exponential function $$C\ e^{\Delta E/RT} \quad (3)$$

wherein ΔE is the net heat of adsorption. The net heat of adsorption is the heat of adsorption of the first layer of molecules minus the heat of condensation of succeeding layers. The inventors hereof have recognized that ΔE, the net heat of adsorption which can be determined from the BET constant C, can be correlated with the number of residual surface polar groups, for example surface hydroxyl groups. Therefore, the method provides a means for correlating the degree of hydrophobicity of an inorganic material with the BET constant C.

Thus, C is inversely proportional to the level of surface treatment of the inorganic material. This is based on the observation that the major contribution to the energy of nitrogen adsorption on a typical material surface is the polar sites, for example hydroxyl sites. The more treated or hydrophobic the material is, the smaller is the heat of monolayer adsorption on the surface of the material. In a particular embodiment of the present invention it has been found that for fumed silica, in which all the isolated and geminal silanol sites have been treated with hydrophobic groups, the BET C constant is typically 26–33 based on nitrogen adsorption. Commercially available treated fillers can be carefully correlated using this technique to determine the level of silanol removal.

In the practice of the present invention, isotherm data are generated over a relative pressure $(P_S/P_O)$ from about 0.05 to about 0.3 and are treated using the BET equation. The constant C is calculated graphically from a straight line having a correlation coefficient of at least 0.99, wherein the slope is $(C-1)/V_M C$ and intercept is $1/V_M C$. The degree of hydrophobicity of the inorganic material may be determined by comparing the BET constant C value with a calibration curve in which the BET constant C has been previously plotted against a conveniently determined parameter proportional to the surface polarity. For example, a calibration curve may be constructed from a plot of BET constant C against % carbon analysis, $^1H$ NMR spectroscopic parameter, $^{29}Si$ CP/MAS NMR spectroscopic parameter, and like parameters. The particular parameter against which BET constant C is plotted in the calibration curve is not critical; it need simply represent an independent method for determining surface polarity. In one embodiment of the present invention the inorganic material is silica, and the degree of surface hydrophobicity of any silica sample is determined by comparison of its BET C value to a calibration curve constructed by plotting BET C values vs. % carbon values determined for a series of silica samples surface treated (for example, silylated) with different levels of a carbon-containing agent to react with silica surface hydroxyl groups. For convenience a calibration curve based on a plot of BET C value against, for example, % carbon value may be converted to a calibration curve of BET C value versus some other parameter more representative of surface polarity, such as number of residual hydroxyl groups per square nanometer.

Accurate determination of BET constant C depends on accurate sample preparation, which requires weighing to ±0.001 g, and on the removal of impurities or adsorbed materials not chemically bonded to the filler surface. This is done by outgassing the sample at a suitable temperature and time before analysis. A suitable treatment is storing the sample under vacuum (at about 0.0001 mm Hg) for 1–3 hours at 200–300° C., which eliminates physically adsorbed materials.

The invention is further illustrated by the follow non-limiting examples. A Coulter Instrument, model SA3100, apparatus was used to measure adsorption-desorption isotherms of particulate materials. EXAMPLE 1

A 0.1160 g sample of fumed silica (about 200 m²/g with a non-porous, mean primary particle diameter of 13.6 nanometers), treated with octamethylcyclotetrasiloxane ($D_4$) at 270° C., 1 atm in accordance with U.S. Pat. No 5,652,017 to Osaheni et al. and the references cited therein, was weighed into a Coulter's SA3100 sample tube. A glass rod was inserted into the tube to minimize the dead space above the sample. The sample was outgassed at 300° C. under dynamic vacuum (about 0.0001 mm Hg) for 1 hour. Helium gas was used to measure the free space in the tube. Type II isotherm data was generated over $P_S/P_O$ of 0.0–0.3 on the sample at 77° K, using nitrogen as the adsorbate. The BET constant C was calculated from the linear portion of the isotherm using equation (1) and found to be 29.02, and the surface area was 176.2 m²/g.

EXAMPLE 2

Figure 2:
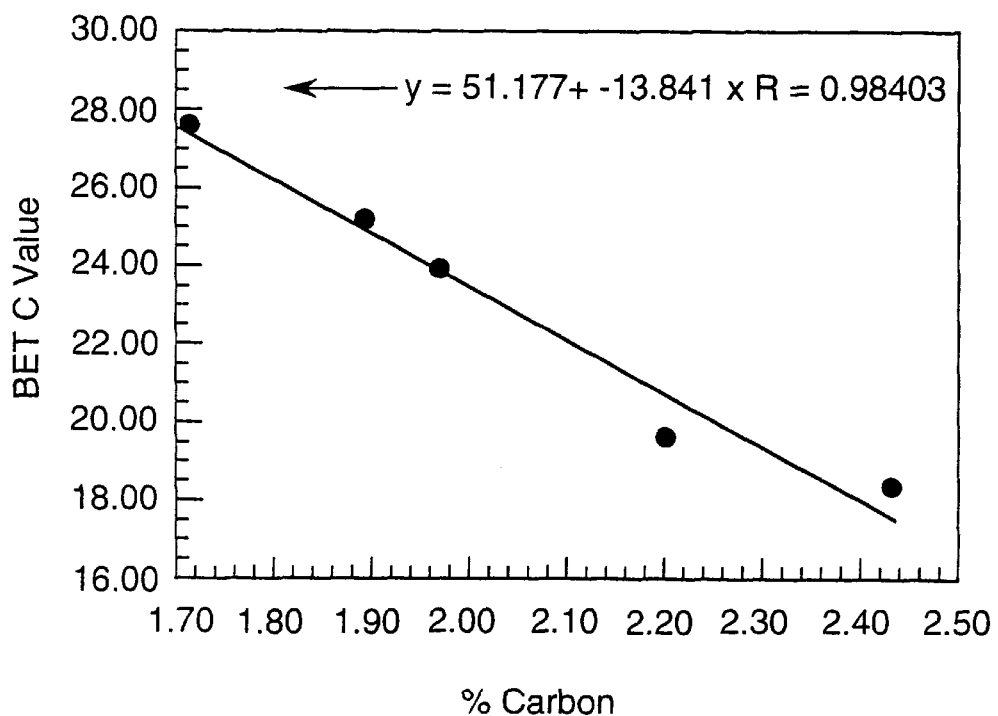
FIG. 2 is a graph illustrating a correlation between BET constant C and percent carbon of five samples of trimethyl silylated fumed silica.

In order to show a correlation between BET C values and the % carbon of the samples, five samples of fumed silica (about 200 m²/g surface area), treated with increasing quantities of hexamethyldisilazane (HMDZ), were analyzed as in Example 1. Unlike $D_4$ treatment, HMDZ silylates each Si—OH site on the filler surface with distinct trimethylsilyl (TMS) groups. Elemental analysis for carbon therefore yields an accurate determination of the number of treated sites, which can be used to determine the number of residual surface hydroxyls. FIG. 2 is a graph illustrating a correlation between BET constant C and percent carbon, and hence residual hydroxyls.

EXAMPLE 3

Figure 3:
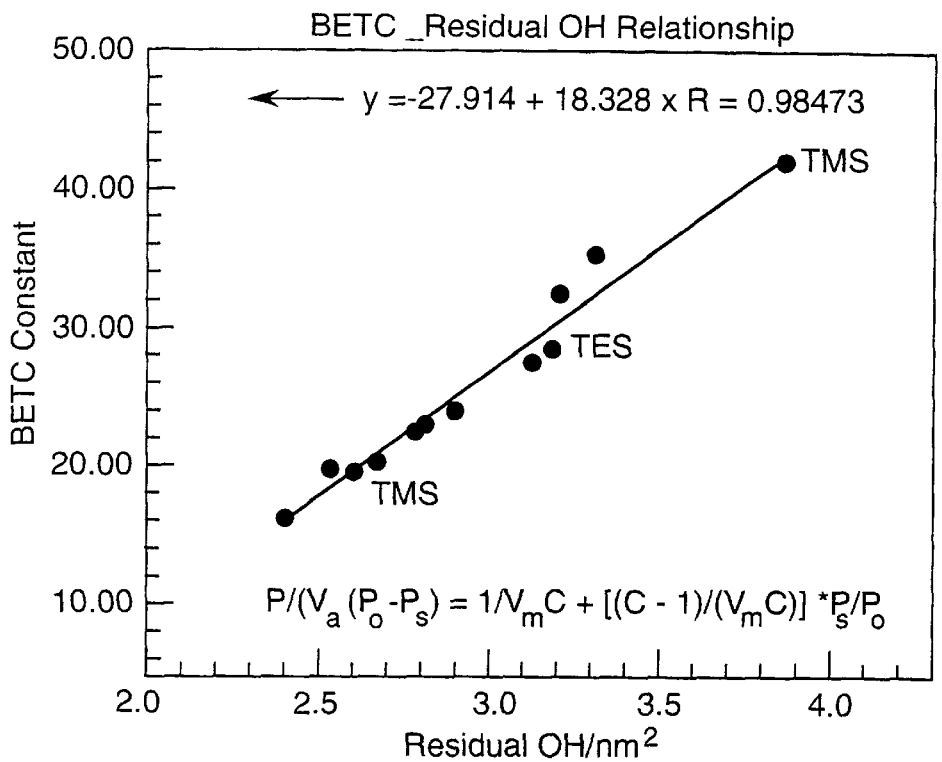
FIG. 3 is a graph showing the correlation of surface hydroxyls with BET constant C.

In order to show the correlation of residual surface hydroxyls with BET constant C, the process of example 2 was repeated whereby a fumed silica having about 200 m²/g was treated with a triethylsilanol silylating agent, yielding triethylsilyl (TES) groups on the surface of the filler as described in U.S. Pat. No. 5,623,028 to Fitzgerald et al., which is incorporated herein by reference. The extent of treatment was determined by carbon elemental analysis from which the concentration of residual hydroxyl groups was determined. The result was correlated with the BET C constant based on nitrogen adsorption as shown in FIG. 3. A linear fit with correlation R of 98.5% or $R^2$ of 97% indicates an excellent fit of the data. This is a calibration curve for relating the residual surface hydroxyls to the BET C constant.

EXAMPLE 4

Figure 4:
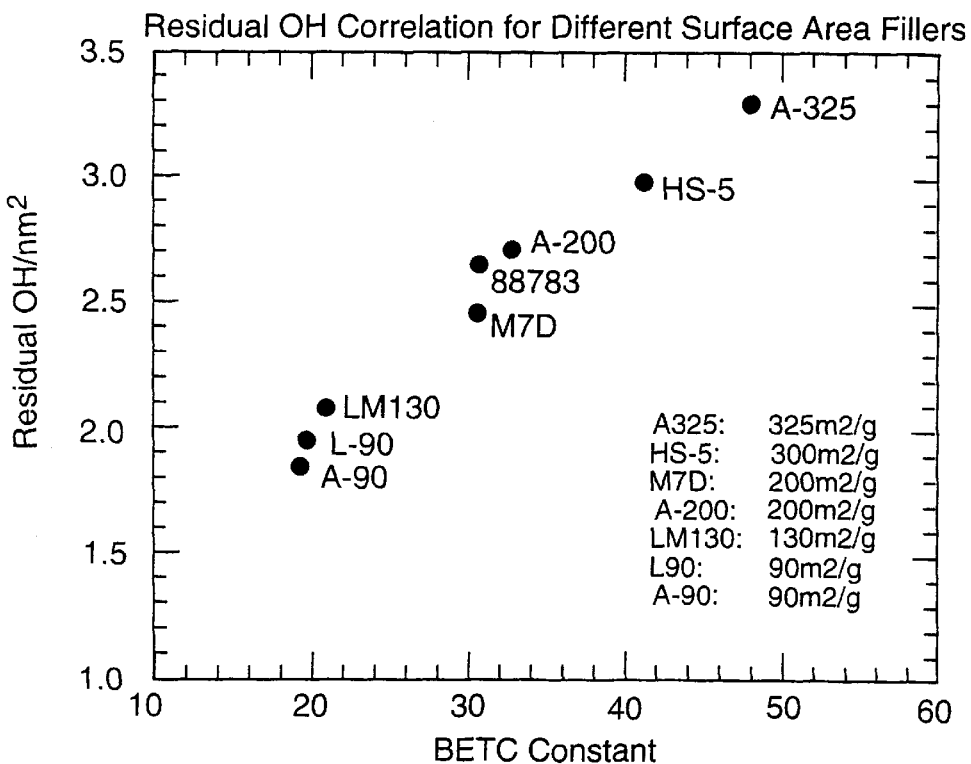
FIG. 4 is a graph showing the residual hydroxyl correlation for different surface area fillers.

Fumed silica samples having different surface areas (from about 90 $m^2/g$ to about 330 $m^2/g$), commercially available from Cabot or Degussa, were treated with hexamethyldisilazane (HMDZ) in accordance with U.S. Pat. No. 5,652,017 to Osaheni et al., which is incorporated herein by reference, by using 5% HMDZ and carrying out the reaction at 150° C. Again, the residual hydroxyl content derived from elemental analysis for carbon was proportional to the BET constant C as shown in FIG. 4.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for determining surface polarity of an inorganic material, comprising:
   determining the net heat of adsorption of an inert gas on the material's surface; and
   correlating the determined net heat of adsorption with the concentration of polar groups on the material's surface.

2. The method of claim 1 wherein the net heat of adsorption is determined by determining the BET constant C for the inorganic material.

3. The method of claim 2, wherein the BET constant C is determined by measuring the volume of the inert gas adsorbed, the sample pressure, and the saturation pressure; plotting the function $$\frac{P_s}{V_A(P_0 - P_s)} \quad (2)$$

versus $(P_S/P_O)$; wherein
   $V_A$ is the volume of gas adsorbed,
   $P_S$ is sample pressure, and
   $P_O$ is the saturation pressure;
and calculating the BET constant C from a straight line having the slope $(C-1)/V_M C$ and intercept $1/V_M C$.

4. The method of claim 3, wherein the measurement is at 77° K.

5. The method of claim 1, wherein said inert gas is selected from the group consisting of argon, krypton, helium, carbon monoxide, and nitrogen.

6. The method of claim 5, wherein said inert gas is nitrogen.

7. The method of claim 1, wherein the inorganic material is selected from the group consisting of precipitated silica, titania, powdered glass, silicates, alumina, asbestos, barium sulfate, zinc oxide, ferric oxide, zinc sulfide, and fumed silica.

8. The method of claim 7, wherein the inorganic material is fumed silica.

9. The method of claim 1, wherein the inorganic material has been surface-treated to change its polarity.

10. The method of claim 9, wherein the treatment is silylation of surface hydroxyl groups with hydrophobic moieties.

11. The method of claim 1, wherein the inorganic material has a surface area from about 0.1 $m^2/g$ to about 450 $m^2/g$.

12. A method for determining hydrophobicity of particulate silica, comprising
   determining the net heat of adsorption of an inert gas on the silica surface; and
   correlating the determined net heat of adsorption with the concentration of hydroxyl groups on the silica surface.

13. The method of claim 12 wherein the net heat of adsorption is determined by determining the BET constant C for the particulate silica.

14. The method of claim 13, wherein the BET constant C is determined by measuring the volume of the nitrogen gas adsorbed, the sample pressure, and the saturation pressure; plotting the function $$\frac{P_s}{V_A(P_0 - P_s)} \quad (2)$$

versus $(P_S/P_O)$; wherein
   $V_A$ is the volume of gas adsorbed,
   $P_S$ is sample pressure, and
   $P_O$ is the saturation pressure;
and calculating the BET constant C from a straight line having the slope $(C-1)/V_M C$ and intercept $1/V_M C$.

15. The method of claim 12, wherein the silica surface is at least partially silylated.

16. The method of claim 12, wherein the inert gas is nitrogen.

* * * * *